United States Patent [19]

Lutomski et al.

[11] Patent Number: 4,895,871

[45] Date of Patent: Jan. 23, 1990

[54] BENZOHETEROCYCLYL KETONE HYDRAZONE INSECTICIDES

[75] Inventors: Kathryn A. Lutomski, Hightstown; Angelina J. Duggan, Lawrenceville, both of N.J.; John F. Engel, Washington Crossing, Pa.

[73] Assignee: FMC Corporation, Philadelphia, Pa.

[21] Appl. No.: 225,519

[22] Filed: Jul. 28, 1988

[51] Int. Cl.⁴ .................... A01N 43/08; C07D 307/87
[52] U.S. Cl. ...................................... 514/469; 549/462
[58] Field of Search .......................... 549/462; 514/469

[56] References Cited

U.S. PATENT DOCUMENTS

| | | | |
|---|---|---|---|
| 3,549,767 | 12/1970 | Esser et al. | 424/327 |
| 3,732,307 | 5/1973 | Middleton | 260/566 B |
| 3,885,042 | 5/1975 | Mulder et al. | 424/323 |
| 4,331,680 | 5/1982 | Giles et al. | 424/303 |
| 4,344,893 | 8/1982 | Copping et al. | 260/456 A |
| 4,394,387 | 7/1983 | Copping et al. | 424/300 |
| 4,432,994 | 2/1984 | Giles et al. | 424/300 |

*Primary Examiner*—Nicky Chan
*Attorney, Agent, or Firm*—Robert L. Andersen; H. Robinson Ertelt

[57] ABSTRACT

Benzoheterocyclyl ketone hydrazones of the formula

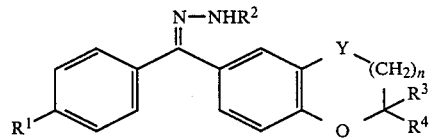

in which Y is methylene, difluoromethylene or oxygen and n is 0 or 1, compositions thereof and their use as insecticides are disclosed and exemplified.

9 Claims, No Drawings

BENZOHETEROCYCLYL KETONE HYDRAZONE INSECTICIDES

The present invention relates to novel N′-(substituted phenyl)(benzoheterocyclyl) ketone hydrazone compounds useful for control of insects, insecticidal compositions thereof, and a method of controlling insects utilizing such compounds.

Various benzophenone hydrazones and their use as insecticides have been reported in the patent and technical literature. For example, U.S. Pat. Nos. 4,331,680, 4,432,994, 4,344,893, 4,394,387, 3,885,042 and 3,732,307 disclose, inter alia, a wide variety of compounds having a generalized formula

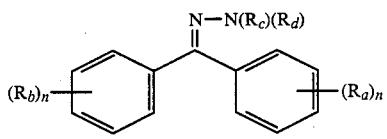

which are said to be useful as insecticides, acaricides, and/or nematicides depending on the particular substitution pattern.

The present invention provides benzoheterocyclyl ketone hydrazones of the formula

in which:

$R^1$ is selected from halogen, preferably chloro or fluoro, hydroxy, methylsulfonyloxy and trifluoromethylsulfonyloxy;

$R^2$ is selected from alkyl, alkylcarbonyl, alkylsulfonyl, ethoxycarbonyl, halophenyl, halophenylaminocarbonyl, halophenylcarbonyl, hydrogen, methylphenylcarbonyl, nitrophenylaminocarbonyl, nitrophenylcarbonyl, phenoxycarbonyl, phenyl, phenylcarbonyl, phenylsulfonyl, trifluoromethylcarbonyl or difluoroethenylalkylcarbonyl;

$R^3$ and $R^4$ are selected from halogen, preferably fluoro, hydrogen, and methyl;

Y is methylene, difluoromethylene, or oxygen; and n is 0 or 1.

Thus, the invention relates to compounds in which the benzoheterocyclyl group is a benzofuranyl group of the formula

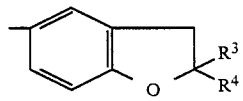

a 1,3-benzodioxolyl group of the formula

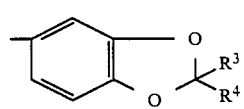

a 1,4-benzodioxanyl group of the formula

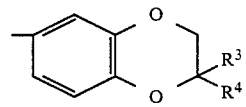

or a group of the formula

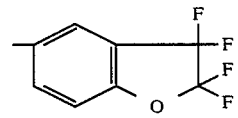

More particularly, the invention relates to compounds of formula I above in which:

A. Y is methylene, n is 0, $R^3$ and $R^4$ are methyl; $R^1$ is chloro, fluoro, methylsulfonyloxy, or trifluoromethylsulfonyloxy; and $R^2$ is selected from hydrogen, $C_1$-$C_3$ alkylcarbonyl, phenylcarbonyl, halophenylcarbonyl, ethoxycarbonyl, 4-chlorophenylaminocarbonyl, phenylsulfonyl, phenoxycarbonyl, 4-methylphenylcarbonyl, formyl, and trifluoromethylcarbonyl; or B. Y is oxygen, n is 0, $R^3$ and $R^4$ are hydrogen or fluoro; $R^1$ is trifluorosulfonyloxy, chloro, or methylsulfonyloxy; and $R^2$ is selected from hydrogen, $C_1$-$C_3$ alkylcarbonyl, ethoxycarbonyl, formyl, trifluoromethylcarbonyl, difluoroethenylalkylcarbonyl, 4-chlorophenylaminocarbonyl, and 4-nitrophenylaminocarbonyl;

C. Y is oxygen, n is 1, $R^3$ and $R^4$ are hydrogen; $R^1$ is chloro; and $R^2$ is selected from $C_1$-$C_3$ alkylcarbonyl and ethoxycarbonyl;

D. Y is difluoromethylene, n is 0, $R^1$ is methylsulfonyloxy or trifluoromethylsulfonyloxy, $R^3$ and $R^4$ are fluoro, and $R^2$ is $C_1$-$C_3$ alkylcarbonyl or formyl.

In the foregoing description and throughout the specification and claims, unless a contrary intent is clearly expressed, the terms described in this paragraph have the meanings described below. Alkyl means a saturated straight, branched, or cyclic hydrocarbon chain of 1–9 carbon atoms; "lower" as applied to alkyl means 1–4, preferably 1–2 carbon atoms; halogen or halo, alone or modifying other components of a molecule means bromine, chlorine or fluorine. In the structures shown below, the designation "c" preceding an alkyl group indicates a cycloalkyl group, and "Ph" designates a phenyl ring.

Specific examples of the foregoing compounds are shown in Table 1 below:

TABLE 1

| Compound Number | $R^1$ | $R^2$ | $R^3, R^4$ | Melting Point (°C.) |
|---|---|---|---|---|
| Y = —CH$_2$—, n = 0 | | | | |
| 1 | Cl | H | CH$_3$ | oil |
| 2 | Cl | C(O)CH$_3$ | CH$_3$ | 144–147 |
| 3 | Cl | —C(O)cPropyl | CH$_3$ | 194–198 |
| 4 | Cl | C(O)Ph, 4-Cl | CH$_3$ | 159–163 |
| 5 | Cl | C(O)OC$_2$H$_5$ | CH$_3$ | 147–149 |
| 6 | Cl | C(O)Ph | CH$_3$ | 124–128 |

TABLE 1-continued $$\underset{R^1}{\overset{N-NHR^2}{\underset{\phantom{x}}{\text{Ph-C-Ph}}}}\text{-}\underset{O}{\overset{Y(CH_2)_n}{\underset{\phantom{x}}{\text{-}}}}\overset{R^3}{\underset{R^4}{\text{C}}}$$

| Compound Number | R¹ | R² | R³, R⁴ | Melting Point (°C.) |
|---|---|---|---|---|
| 7 | Cl | C(O)NHPh, 4-Cl | CH₃ | 187–190 |
| 8 | Cl | S(O)₂Ph | CH₃ | 128–132 |
| 9 | F | C(O)CH₃ | CH₃ | 127–131 |
| 10 | F | C(O)cPropyl | CH₃ | 151–167 |
| 11 | F | C(O)Ph | CH₃ | 129–132 |
| 12 | F | C(O)OC₂H₅ | CH₃ | 152–156 |
| 13 | F | C(O)OPh | CH₃ | 178–182 |
| 14 | OS(O)₂CH₃ | H | CH₃ | 57–60 |
| 15 | OS(O)₂CH₃ | C(O)OC₂H₅ | CH₃ | 108–112 |
| 16 | OS(O)₂CF₃ | H | CH₃ | oil |
| 17 | OS(O)₂CF₃ | C(O)CH₃ | CH₃ | 155–158 |
| 18 | OS(O)₂CF₃ | C(O)cPropyl | CH₃ | 144–146 |
| 19 | OS(O)₂CF₃ | C(O)Ph, 4-Cl | CH₃ | 146–151 |
| 20 | OS(O)₂CF₃ | C(O)Ph, 4-CH₃ | CH₃ | 64.5–65; 74.5–75 |
| 21 | OS(O)₂CF₃ | C(O)OC₂H₅ | CH₃ | 70–73 |
| 22 | OS(O)₂CF₃ | C(O)OPh | CH₃ | glass |
| 23 | OS(O)₂CF₃ | —CHO | CH₃ | 138–142; 160–163 |
| 24 | OS(O)₂CF₃ | C(O)Ph, 3,4-Cl | CH₃ | 75–80 |
| 25 | OS(O)₂CF₃ | —C(O)CF₃ | CH₃ | oil |
| Y = O, n = 0 | | | | |
| 26 | OS(O)₂CF₃ | H | H | 75–77 |
| 27 | OS(O)₂CF₃ | C(O)CH₃ | H | 103–130 |
| 28 | OS(O)₂CF₃ | C(O)OC₂H₅ | H | oil |
| 29 | OS(O)₂CF₃ | —CHO | H | solid/oil emulsion |
| 30 | OS(O)₂CF₃ | —C(O)cPropyl | H | 139–149 |
| 31 | OS(O)₂CF₃ | C(O)CF₃ | H | 98.5–115 |
| 32 | OS(O)₂CF₃ | C(O)(CH₂)₉CH=CF₂ | H | wax |
| 33 | Cl | C(O)OC₂H₅ | F | 123–126 |
| 34 | Cl | C(O)NHPh, 4-Cl | F | 168–171 |
| 35 | Cl | C(O)NHPh, 4-NO₂ | F | 179–183 |
| 36 | OS(O)₂CH₃ | H | F | oil |
| 37 | OS(O)₂CH₃ | C(O)CH₃ | F | 155–159 |
| 38 | OS(O)₂CH₃ | C(O)OC₂H₅ | F | 160–171 |
| 39 | OS(O)₂CH₃ | C(O)NHPh, 4-NO₂ | F | 268–272 |
| 40 | OS(O)₂CF₃ | H | F | oil |
| 41 | OS(O)₂CF₃ | C(O)CH₃ | F | 169–174 |
| 42 | OS(O)₂CF₃ | C(O)NHPh, 4-NO₂ | F | >272 |
| Y = O, n = 1 | | | | |
| 43 | Cl | C(O)CH₃ | H | 135–139 |
| 44 | Cl | C(O)OC₂H₅ | H | 142–146 |
| Y = CF₂, n = 0 | | | | |
| 45 | OS(O)₂CF₃ | CHO | F | 195–198 |
| 46 | OS(O)₂CH₃ | C(O)CH₃ | F | 175–181 |

The syntheses of the compounds of the present invention were accomplished by methods known to those skilled in the art. Briefly, certain compounds wherein Y is methylene, n is 0, and R³, R⁴ are methyl, were prepared stepwise commencing with the reaction of either 4-chloro-4'-hydroxybenzophenone or 4,4'-dihydroxybenzophenone with 3-chloro-2-methylpropene in the presence of potassium carbonate in dimethylsulfoxide to afford the corresponding 4-chloro- or 4-hydroxy-4'-(2-methyl-2propenoxy)benzophenone. When R¹ is methylsulfonyloxy or trifluoromethylsulfonyloxy, the 4-hydroxy-4'-(2-methyl-2-propenoxy)benzophenone was reacted with methanesulfonyl chloride or trifluoromethanesulfonic anhydride, in the presence of pyridine, to afford the corresponding 4-methylsulfonyloxy-or 4-trifluoromethylsulfonyloxy-4'-(2-methyl-2-propenoxy)-benzophenone. The resulting 4-substituted-4'-(2-methyl-2-propenoxy)benzophenones were cyclized using magnesium chloride to yield the appropriate (4-substituted-phenyl)(2,3-dihydro-2,2-dimethyl-benzofuran-5-yl) ketone, which was in turn reacted with hydrazine hydrate and acetic acid to afford the intermediate (4-substituted-phenyl)(2,3-dihydro-2,2-dimethyl-benzofuran-5-yl) ketone hydrazone (I). Reaction of (I) with the appropriate isocyanate or acid chloride yielded the target N'-substituted (4-substituted-phenyl)(2,3-dihydro-2,2-dimethylbenzofuran-5-yl) ketone hydrazones of the present invention. Example 1 below illustrates this route.

In an alternate route to those compounds wherein Y is methylene, n is 0, and R³, R⁴ are methyl, 2,3-dihydro-2,2-dimethylbenzofuran was brominated in carbon tetrachloride to afford the corresponding 5-bromo-2,3-dihydro 2,2-dimethylbenzofuran. The 5-bromo intermediate was reacted with n-butyllithium at −78° C. in tetrahydrofuran and the product treated with the appropriate 4-substituted benzaldehyde to yield α-(4-substituted-phenyl)-(2,3-dihydro-2,2-dimethylbenzofuran-5-yl)methanol. The resulting methanol was then reacted with Jones reagent in acetone to yield the corresponding (4-substituted-phenyl)(2,3-dihydro-2,2-dimethylbenzofuran-5-yl) ketone. The ketone was then reacted with hydrazine hydrate by the method previously described to yield the hydrazone (I). Example 2 illustrates this route.

Certain compounds wherein Y is oxygen, n is 0, and R¹, R² are fluoro, were prepared in the following manner. The intermediate, 3,4-difluoromethylenedioxybenzoic acid was synthesized by dichlorination of benzodioxole in the 2-position with phosphorus pentachloride, halogen exchange using potassium fluoride in the presence of 1,4,7,10,13,16-hexaoxacyclooctadecane (18-crown-6) in adiponitrile, and bromination using iron powder in carbon tetrachloride to afford the 5-bromo-2,2-difluoro-1,3-benzodioxole intermediate. This intermediate was then reacted with n-butyllithium and carbon dioxide in diethyl ether to yield 3,4-difluoromethylenedioxybenzoic acid. The resulting acid was treated as outlined above to afford the hydrazone (I). Example 3 illustrates this route.

In an alternate method to those compounds wherein Y is oxygen, n is 0, and R³, R⁴ are fluorine, the 5-bromo-2,2-difluoro-1,3-benzodioxole intermediate described above was reacted with the appropriate 4-substituted benzaldehyde at -78° C. in the presence of n-butyllithium in tetrahydrofuran to yield the corresponding α-(4-substituted-phenyl)(2,2-difluoro-1,3-benzodioxol-5-yl)methanol. The resulting alcohol was then treated with Jones reagent in acetone as described above to afford the corresponding ketone. The ketone was then reacted with hydrazine hydrate as described above to yield the hydrazone (I). This is analogous to that shown in Example 2, differing only in the alcohol used.

When the substituent R¹ was methylsulfonyloxy or trifluoromethylsulfonyloxy, a number of additional synthesis steps were needed to obtain the hydrazone (I). The intermediate 4-hydroxybenzaldehyde was reacted with (1,1-dimethylethyl)dimethylsilyl chloride and imidazole in dimethylformamide to afford 4-[(1,1-dimethylethyl)dimethylsilyloxy]benzaldehyde. With the hydroxy substituent protected, the benzaldehyde was reacted by methods described above with the 5-bromo-2,2-difluoro-1,3-benzodioxole to afford the corresponding alcohol which was in turn converted to the ketone. Reaction of the resulting [[4-(1,1-dimethylethyl)dimethylsilyloxy]phenyl](2,2-difluoro-1,3-benzodioxol-5-yl)

ketone with tetrabutylammonium fluoride in tetrahydrofuran cleaved the (1,1-dimethylethyl)dimethylsilyl substituent to yield (4-hydroxyphenyl)(2,2-difluoro-1,3-benzodiox-5-yl) ketone. The 4-hydroxy intermediate was reacted with methanesulfonyl chloride or trifluoromethanesulfonic anhydride by methods described above to yield the corresponding (4-methylsulfonyloxyphenyl)- or (4-trifluoromethylsulfonyloxyphenyl)(2,2-difluoro-1,3-benzodioxol-5yl) ketone. The ketone was then converted to the hydrazone (I) as described above. Example 4 illustrates this route.

The following preparatory examples illustrate these methods:

EXAMPLE 1

Synthesis of (E/Z)-N'-ethoxycarbonyl (4-trifluoromethylsulfonyloxyphenyl)(2,3-dihydro-2,2-dimethylbenzofuran-5-yl) ketone hydrazone (Compound 21)

Step A: Synthesis of 4-hydroxy-4'-(2-methyl-2-propenoxy)benzophenone as an intermediate A solution of 14.6 grams (0.0682 mole) of 4,4'-dihydroxybenzophenone and 10.4 grams (0.0751 mole) of potassium carbonate in 250 mL of dimethyl sulfoxide was stirred under a nitrogen atmosphere for 20 minutes. To this was added during a 20 minute period via syringe 7.32 mL (0.0751 mole) of 3-chloro-2-methylpropene. Upon completion of addition the reaction mixture was heated at 60°–65° C. for 18 hours. The reaction mixture was poured into 600 mL of ice-water and then was extracted with four portions of diethyl ether. The combined ether extracts were washed with two 200 mL portions of aqueous 1N sodium hydroxide. The combined sodium hydroxide washes were made acidic with aqueous 20% hydrochloric acid. The resultant solid was dissolved in diethyl ether, and the solution was washed first with a saturated aqueous sodium chloride solution and then with water. The organic layer was dried with magnesium sulfate and filtered. The filtrate was concentrated under reduced pressure to yield 8.6 grams of 4-hydroxy-4'-(2-methyl-2-propenoxy)benzophenone.

Step B: Synthesis of 4-(trifluoromethylsulfonyloxy)-4'-(2-methyl-2-propenoxy)benzophenone as an intermediate A solution of 3.3 grams (0.0124 mole) of 4-hydroxy4'-(2-methyl-2-propenoxy)benzophenone in 50 mL of methylene chloride was stirred under a nitrogen atmosphere and cooled to −25° C. To this was added 2.2 mL (0.0273 mole) of pyridine followed by 4.2 mL of trifluoromethanesulfonic anhydride, both via syringe. Upon completion of addition the reaction mixture was stirred at −25° C. for one hour and then was quenched with 10 mL of methanol. The reaction mixture was poured into 150 mL of ice-water. Methylene chloride, 50 mL, was added, and the mixture was placed in a separatory funnel. The mixture was shaken, and the organic layer was separated. The organic layer was washed with water and then with a cold saturated, aqueous solution of potassium dihydrogen phosphate. The organic layer was dried with magnesium sulfate and filtered. The filtrate was concentrated under reduced pressure to yield 4.6 grams of 4-(trifluoromethylsulfonyloxy)-4'-(2-methyl-2-propenoxy)benzophenone as a solid. The nmr spectrum was consistent with the proposed structure.

Step C: Synthesis of (4-trifluoromethylsulfonyloxyphenyl)(2,3-dihydro-2,2-dimethylbenzofuran-5-yl) ketone as an intermediate A mixture of 4.4 grams (0.011 mole) of 4-(trifluoromethylsulfonyloxy)-4'-(2-methyl-2-propenoxy)-benzophenone and 0.05 gram (0.0005 mole) of magnesium chloride was stirred under a nitrogen atmosphere at 170°–175° C. for 20 hours. The reaction mixture was cooled to ambient temperature, and diethyl ether was added. The mixture was filtered through diatomaceous earth, and the filtrate was placed in a separatory funnel and washed with two portions of aqueous 0.5 N sodium hydroxide, three portions of water, and one portion of a saturated, aqueous, sodium chloride solution. The organic layer was dried with sodium sulfate and filtered. The filtrate was concentrated under reduced pressure to a residue. The residue was purified by centrifically accelerated, radial thin layer chromatography. Elution was accomplished using 3:1 methylene chloride:hexane. The appropriate fractions were combined and concentrated under reduced pressure to yield 1.7 grams of (4-trifluoromethylsulfonyloxyphenyl)(2,3-dihydro-2,2-dimethylbenzofuran-5-yl) ketone. The nmr spectrum was consistent with the proposed structure.

Step D: Synthesis of (4-trifluoromethylsulfonyloxyphenyl)(2,3-dihydro-2,2-dimethylbenzofuran-5-yl) ketone hydrazone as an intermediate (Compound 16)

A mixture of 1.6 grams (0.004 mole) of (4-trifluoromethylsulfonyloxyphenyl)(2,3-dihydro-2,2-dimethylbenzofuran-5-yl) ketone in 75 mL of ethanol was stirred, and 0.6 mL (0.0121 mole) of hydrazine hydrate followed by 0.5 mL of acetic acid were both added via syringe. Upon completion of addition the reaction mixture was heated at reflux for 7 hours and then was allowed to cool to ambient temperature where it was stirred for 18 hours. The reaction mixture was concentrated under reduced pressure, and the residue was stirred with diethyl ether and water. The mixture was placed in a separatory funnel, and the layers were separated. The organic layer was washed with aqueous 10% sodium hydroxide solution, two portions of water, and with a saturated, aqueous solution of sodium chloride. The organic layer was concentrated under reduced pressure to yield 1.6 grams of (4-trifluoromethylsulfonyloxyphenyl)(2,3-dihydro-2,2-dimethylbenzofuran-5-yl) ketone hydrazone as an oil. The nmr spectrum was consistent with the proposed structure.

Step E: Synthesis of (E/Z)-N'-ethoxycarbonyl (4-trifluoromethylsulfonyloxyphenyl)(2,3-dihydro-2,2-dimethylbenzofuran-5-yl) ketone hydrazone (Compound 21)

A solution of 1.0 gram (0.0024 mole) of (4-trifluoromethylsulfonyloxyphenyl)(2,3-dihydro-2,2-dimethylbenzofuran-5-yl) ketone hydrazone in 50 mL of diethyl ether was stirred, and 0.22 mL (0.0027 mole) of pyridine followed by 0.26 mL (0.0027 mole) of ethyl chloroformate were both added via syringe. Upon completion of addition the reaction mixture was stirred at ambient temperature for six hours. The reaction mixture was filtered, and the filtrate was concentrated under reduced pressure to a residue. The residue was subjected to centrifically accelerated, radial thin layer chromatography. Elution was accomplished using 19:1 methylene chloride: ethyl acetate. The appropriate fractions were combined and concentrated under reduced pressure to yield 0.81 gram of (E/Z)-N'-ethoxycarbonyl (4-trifluoromethylsulfonyloxyphenyl)(2,3-dihydro-2,2-dimethylbenzofuran-5-yl) ketone hydrazone, m.p. 70°–73° C. The nmr spectrum was consistent with the proposed structure.

Analysis calcd for $C_{21}H_{21}F_3N_2O_6S$: C 51.85; H 4.35; N 5.76; Found: C 52.02; H 4.10; N 5.72.

EXAMPLE 2

Synthesis of (4-chlorophenyl)-2,3-dihydro-2,2-dimethylbenzofuran-5-yl) ketone hydrazone (Compound 1)

Step A: Synthesis of 5-Bromo-2,3-dihydro-2,2-dimethylbenzofuran as an intermediate The reaction vessel was wrapped with aluminum foil to keep out light and a solution of 30.9 grams (0.209 mole) of 2,3-dihydro-2,2-dimethylbenzofuran in 500 mL of carbon tetrachloride was added to it. Under a nitrogen atmosphere the stirred solution was warmed to reflux and a solution of 11 mL of bromine in 25 mL of carbon tetrachloride was added dropwise during a 30 minute period. Upon completion of addition the reaction mixture was stirred at reflux for 18 hours. After this time the reaction mixture was cooled to ambient temperature and was washed with three portions of an aqueous solution saturated with sodium chloride. The organic layer was dried with sodium sulfate and filtered. The filtrate was concentrated under reduced pressure to yield 46.1 grams of product that was 93% 5-bromo-2,3-dihydro-2,2dimethylbenzofuran.

Step B: Synthesis of α-(4-chlorophenyl)-(2,3-dihydro-2,2-dimethylbenzofuran-5-yl)methanol as an intermediate Under a nitrogen atmosphere, a solution of 4.4 grams (0.019 mole) of 5-bromo-2,3-dihydro-2,2-dimethylbenzofuran in 40 mL of dry tetrahydrofuran was cooled to −78° C., and 8.93 mL (0.019 mole) of 2.2 Molar n-butyllithium (in hexanes) was added via syringe. Upon completion of addition, the reaction mixture was stirred at −78° C. for 80 minutes.

In a second reaction vessel, a solution of 2.7 grams (0.019 mole) of 4-chlorobenzaldehyde in 40 mL of dry tetrahydrofuran was cooled to 0° C. The benzofuran anion was then added dropwise via pressure gradient to the stirred aldehyde solution using a two-tipped needle connecting the reaction vessels. Upon completion of addition the reaction mixture was stirred at 0° C. for 15 minutes, and then it was allowed to warm to ambient temperature where it stirred under a nitrogen atmosphere for 18 hours. The reaction mixture was quenched with 30 mL of an aqueous solution saturated with ammonium chloride. The mixture was placed in a separatory funnel, and the aqueous phase separated. The organic layer was then washed in turn with one portion of an aqueous solution saturated with ammonium chloride, two portions of water and one portion of an aqueous solution saturated with sodium chloride. The organic layer was dried with sodium sulfate and filtered. The filtrate was concentrated under reduced pressure to a residue. The residue was purified by column chromatography on silica gel. Elution was accomplished using 25% acetone in hexane. The appropriate fractions were combined and concentrated under reduced pressure to yield α-(4-chlorophenyl)-(2,3-dihydro-2,2-dimethylbenzofuran-5-yl)methanol. The nmr spectrum was consistent with the proposed structure.

Step C: Synthesis of (4-chlorophenyl) (2,3-dihydro-2,2-dimethylbenzofuran-5-yl) ketone as an intermediate A stirred solution of 1.95 grams (0.007 mole) of α-(4-chlorophenyl)-(2,3-dihydro-2,2-dimethylbenzofuran-2-yl)methanol in 40 mL of acetone was cooled to 0° C., and Jones Reagent was added dropwise by pipette until the reaction mixture stayed red (3 mL in this case). Upon completion of addition the reaction mixture was stirred at 0° C. for 20 minutes, and then it was quenched with 5 mL of 1-methylethanol. The reaction mixture was concentrated under reduced pressure to one-third of its original volume, and 25 mL of water followed by 25 mL of diethyl ether were added. The mixture was placed in a separatory funnel and shaken. The aqueous layer was removed and washed with diethyl ether. The wash was combined with the organic layer, and the combination was washed with two portions of water and one portion of an aqueous solution saturated with sodium chloride. The organic layer was dried with sodium sulfate and filtered. The filtrate was concentrated under reduced pressure to yield 1.4 grams of (4-chlorophenyl) (2,3-dihydro-2,2-dimethylbenzofuran-5-yl) ketone. The nmr spectrum was consistent with the proposed structure.

Step D: Synthesis of (4-chlorophenyl) (2,3-dihydro-2,2-dimethylbenzofuran-5-yl) ketone hydrazone (Compound 1)

This compound was prepared in a manner analogous to that of Example 1, Step D, using 1.4 grams (0.005 mole) of (4-chlorophenyl) (2,3-dihydro-2,2-dimethylbenzofuran-5-yl)ketone, 0.4 mL (0.008 mole) of hydrazine hydrate, and 0.3 mL of acetic acid in 50 mL of ethanol. The yield of (4-chlorophenyl) (2,3-dihydro-2,2-(dimethyl- benzofuran-5-yl) ketone hydrazone was 1.23 grams. The nmr spectrum was consistent with the proposed structure.

EXAMPLE 3

Synthesis of (E/Z)-N'-(4-nitrophenylaminocarbonyl)-(4-chlorophenyl)(2,2-difluoro-1,3-benzodioxol-5-yl) ketone hydrazone (Compound 35)

Step A: Synthesis of 2,2-dichloro-1,3-benzodioxole as an intermediate

A solution of 305.3 grams 2.5 moles) of 1,3-benzodioxole and 1041.2 grams (5.0 moles) of phosphorus pentachloride was stirred and heated at 98°–165° C. for 1.5 hours. The reaction mixture was distilled under reduced pressure to yield 440.5 grams of 2,2-dichloro-1,3-benzodioxole, b.p. 60°–75° C./3.5-4.5 mm.

Step B: Synthesis of 2,2-difluoro-1,3-benzodioxole as an intermediate

A mixture of 300.0 grams (1.57 mole) of 2,2-dichloro-1,3-benzodioxole, 273.7 grams (4.71 mole) of potassium fluoride, and 3.0 grams of 1,4,7,10,13,16-hexaoxacyclooctadecane in 815 mL of adiponitrile was warmed to 120° C. during a 30 minute period. After this time an additional 3.0 grams of 1,4,7,10,13,16-hexaoxacyclooctadecane was added, and the heating was continued at 110° C. for an additional 9.5 hours. The reaction mixture was cooled and distilled under reduced pressure to yield 302.7 grams of 2,2-difluoro-1,3-benzodioxole, b.p. 56°–79° C./114 mm.

Step C: Synthesis of 5-bromo-2,2-difluoro-1,3-benzodioxole as an intermediate A mixture of 15.8 grams (0.1 mole) of 2,2-difluoro-1,3-benzodioxole in 200 mL of carbon tetrachloride was stirred, and 2.8 grams (0.05 mole) of iron powder was added. The reaction mixture was cooled to 0° C., and 5.2 mL (0.1 mole) of bromine was added during a 20 minute period. Upon completion of addition the reaction mixture was cautiously warmed to 75° C. where it was stirred for one hour and then was allowed to cool to ambient temperature where it was stirred for 18 hours. The reaction mixture was taken up in 200 mL water and stirred for 20 minutes. The organic layer was separated and washed with water and then with two portions of an aqueous solution saturated with sodium chloride. The organic layer was dried with magnesium sulfate and filtered. The filtrate was concentrated under reduced pressure to a residue. The residue was distilled under high vacuum to yield 11.7 grams of 5-bromo-2,2-difluoro-1,3-benzodioxole. The nmr spectrum was consistent with the proposed structure. The reaction was repeated several times.

Step D: Synthesis of 3,4-difluoromethylenedioxybenzoic acid as an intermediate A solution of 20.1 grams 0.085 mole) of 5-bromo-2,2-difluoro-1,3-benzodioxoee in 300 mL of diethyl ether was stirred and cooled to −78° C. To this was added dropwise 37 mL (0.088 mole) of n-butyllithium (2.39 Molar in hexane). Upon completion of addition the reaction mixture was stirred for 30 minutes and then was quenched with carbon dioxide in diethyl ether. The reaction mixture was made basic with aqueous 10% sodium hydroxide. The aqueous layer was separated, washed with diethyl ether, and then was made acidic with concentrated hydrochloric acid. The mixture was extracted with methylene chloride, and the extract was dried with sodium sulfate and filtered. The filtrate was concentrated under reduced pressure to yield 16.1 grams of 3,4-difluoromethylenedioxybenzoic acid, m.p. 152°–156° C.

Step E: Synthesis of 3,4-difluoromethylenedioxybenzoyl chloride as an intermediate A solution of 15.0 grams (0.0742 mole) of 3,4-difluoromethylenedioxybenzoic acid in 200 mL of diethyl ether was stirred and cooled to 0° C. To this was added one drop of dimethylformamide followed by the dropwise addition of 11.3 grams (0.0890 mole) of oxalyl chloride. Upon completion of addition the reaction mixture was allowed to warm to ambient temperature where it stirred for 60 hours. After this time the reaction mixture was concentrated under reduced pressure to yield 16.6 grams of 3,4-difluoromethylenedioxybenzoyl chloride.

Step F: Synthesis of N-methyl-N-methoxy-3,4-difluoromethylenedioxybenzamide as an intermediate A solution of 14.4 grams (0.065 mole) of 3,4-difluoromethylenedioxybenzoyl chloride in 150 mL of methylene chloride was stirred and cooled to 0° C. To this was added 6.4 grams (0.066 mole) of O,N-dimethylhydroxylamine hydrochloride, followed by the dropwise addition of 11.0 mL (0.136 mole) of pyridine. Upon completion of addition the reaction mixture was stirred at ambient temperature for 18 hours. The reaction mixture was washed with two portions of aqueous 10% hydrochloric acid, two portions of aqueous IN sodium hydroxide, and two portions of an aqueous saturated solution of sodium chloride. The organic layer was dried with sodium sulfate and filtered. The filtrate was concentrated under reduced pressure to yield 15.1 grams of N-methyl-N-methoxy-3,4-difluoromethylenedioxybenzamide. The nmr spectrum was consistent with the proposed structure.

Step G: Synthesis of (4-chlorophenyl)(2,2-difluoro-1,3-benzodioxol-5-yl) ketone as an intermediate A 1.0 Molar solution of 4-chlorophenyl magnesium bromide in diethyl ether, 32.3 mL (0.0328 mole), was stirred and cooled to 0° C. To this was added dropwise a solution of 7.3 grams (0.0298 mole) of N-methyl-N-methoxy-3,4-difluoromethylenedioxybenzamide in 30 mL of diethyl ether. Upon completion of addition the reaction mixture was allowed to warm to ambient temperature where it was stirred for 18 hours. After this time the reaction mixture was stirred with 30 mL of ammonium chloride solution. The mixture was taken up in diethyl ether and washed with two portions of water and two portions of an aqueous solution saturated with sodium chloride. The organic layer was dried with sodium sulfate and filtered. The filtrate was concentrated under reduced pressure to a residue which was subjected to column chromatography on silica gel. Elution was accomplished with 3:2 methylene chloride:hexane. The appropriate fractions were combined and concentrated under reduced pressure to yield 5.1 grams of (4-chlorophenyl)(2,2-difluoro-1,3-benzodioxol-5-yl) ketone as a solid. The nmr spectrum was consistent with the proposed structure.

Step H: Synthesis of (4-chlorophenyl)(2,2-difluoro-1,3-benzodioxol-5-yl) ketone hydrazone as an intermediate This compound was prepared in a manner analogous to that of Example 1, Step D, using 3.2 grams (0.0109 mole) of (4-chlorophenyl)(2,2-difluoro-1,3-benzodioxol-5-yl) ketone, 2.4 mL (0.0494 mole) of hydrazine hydrate, and 1 mL of acetic acid in 60 mL of ethanol. The yield of (4-chlorophenyl)(2,2-difluoro-1,3-benzodioxol-5-yl) ketone hydrazone was 3.2 g as an oil. The nmr spectrum was consistent with the proposed structure.

Step I: Synthesis of (E/Z)-N'-(4-nitrophenylaminocarbonyl)(4-chlorophenyl)(2,2-difluoro-1,3-benzodioxol-5-yl) ketone hydrazone (Compound 35)

A mixture of 0.80 gram (0.0027 mole) of (4-chlorophenyl) (2,2-difluoro-1,3-benzodioxol-5-yl) ketone hydrazone and 0.61 gram (0.0037 mole) of 4-nitrophenyl isocyanate in 30 mL of diethyl ether was stirred at ambient temperature for 18 hours. The resultant solid was collected by filtration to yield 0.97 gram of (E/Z)-N'-(4-nitrophenylaminocarbonyl) (4-chlorophenyl)(2,2-difluoro-1,3-benzodioxol-5-yl) ketone hydrazone, m.p. 179°-183° C. The nmr spectrum was consistent with the proposed structure.

EXAMPLE 4

Synthesis of (4-trifluoromethylsulfonyloxyphenyl) (2,2-difluoro-1,3-benzodioxol-5-yl) ketone hydrazone (Compound 40)

Step A: Synthesis of 4-[(1,1-dimethylethyl)dimethylsilyloxy]benzaldehyde as an intermediate To a stirred solution of 10.4 grams (0.085 mole) of 4-hydroxybenzaldehyde in 36.5 mL of dimethylformamide was added 15.4 grams (0.102 mole) of (1,1-dimethylethyl)dimethylsilyl chloride and then 14.8 grams (0.218 mole) of imidazole. Upon completion of addition the reaction mixture was stirred under a nitrogen atmosphere at ambient temperature for three hours. The reaction mixture was poured into a separatory funnel, and water was added. The mixture was extracted with diethyl ether. The ether layer was washed in turn with one portion of aqueous 10% sodium hydroxide, one portion of aqueous 10% hydrochloric acid, one portion of water, and one portion of an aqueous solution saturated with sodium chloride. The organic layer was dried with sodium sulfate and filtered. The filtrate was concentrated under reduced pressure to a residue. The residue was dissolved in diethyl ether and was stirred for 20 minutes with decolorizing carbon and neutral alumina. The mixture was filtered through diatomaceous earth, and the filtrate was concentrated under reduced pressure to yield 19.4 grams of 4-[(1,1-dimethylethyl)dimethylsilyloxy]benzaldehyde. The nmr spectrum was consistent with the proposed structure.

Step B: Synthesis of α-[4-[(1,1-dimethylethyl)dimethylsilyloxy]phenyl]-(2,2-difluoro-1,3-benzodioxol-5-yl)methanol as an intermediate This compound was prepared in a manner analogous to that of Example 2, Step B, using 13.9 grams (0.059 mole) of 4-[(1,1-dimethylethyl)dimethylsilyloxy]benzaldehyde, 14.0 grams (0.059 mole) of 5-bromo-2,2-difluoro-1,3-benzodioxole, and 26.6 mL of 2.2 Molar n-butyllithium in 60 mL of diethyl ether. The yield of α-[4-dimethylethyl)dimethylsilyloxy]phenyl](2,2-difluoro1,3-benzodioxol-5-yl)methanol was 22.3 grams. The nmr spectrum was consistent with the proposed structure.

Step C: Synthesis of [4-[(1,1-dimethylethyl)dimethylsilyloxy]phenyl](2,2-difluoro-1,3-benzodioxol-5-yl) ketone as an intermediate This compound was prepared in a manner analogous to that of Example 2, Step C, using 22.3 grams (0.056 mole) of α-[4-[(1,1-dimethylethyl)dimethylsilyloxy]-phenyl](2,2-difluoro-1,3-benzodioxol-5-yl)methanol and Jones Reagent in 100 mL of diethyl ether. The yield of [4-[(1,1-dimethylethyl)dimethylsilyloxy]phenyl](2,2-difluoro-1,3-benzodioxol-5-yl) ketone was 11.4 grams. The nmr spectrum was consistent with the proposed structure.

Step D: Synthesis of 4-hydroxyphenyl (2,2-difluoro-1,3-benzodioxol-5-yl) ketone as an intermediate A solution of 11.4 grams (0.029 mole) of [4-[(1,1dimethylethyl)dimethylsilyloxy]phenyl](2,2-difluoro-1,3-benzodioxol-5-yl) ketone in 50 mL of tetrahydrofuran was stirred, and 13.7 grams (0.044 mole) of tetrabutylammonium fluoride was added. Upon completion of addition the reaction mixture was stirred for ten minutes. After this time the reaction mixture was washed in turn with an aqueous solution saturated with ammonium chloride, water, aqueous dilute hydrochloric acid, and an aqueous solution saturated with sodium chloride. The organic layer was dried with sodium sulfate and filtered. The filtrate was concentrated under reduced pressure to yield 8.0 grams of 4-hydroxyphenyl (2,2-difluoro-1,3-benzodioxol-5-yl) ketone. The nmr spectrum was consistent with the proposed structure.

Step E: Synthesis of (4-trifluoromethylsulfonyloxyphenyl) (2,2-difluoro-1,3-benzodioxol-5-yl) ketone as an intermediate This compound was prepared in a manner analogous to that of Example 1, Step B, using 8.0 grams (0.029 mole) of 4-hydroxyphenyl (2,2-difluoro-1,3-benzodioxol-5-yl) ketone, 10 mL (0.058 mole) of trifluoromethanesulfonic anhydride, and 5 mL (0.063 mole) of pyridine in 50 mL of methylene chloride. The yield of (4-trifluoromethylsulfonyloxyphenyl) (2,2-difluoro-1,3-benzodioxol-5-yl) ketone was 11.9 grams. The nmr spectrum was consistent with the proposed structure.

Step F: Synthesis of (4-trifluoromethylsulfonyloxyphenyl) (2,2-difluoro-1,3-benzodioxol-5-yl) ketone hydrazone (Compound 40)

This compound was prepared in a manner analogous to that of Example 1, Step D, using 11.3 grams (0.028 mole) of (4-trifluoromethylsulfonyloxyphenyl) (2,2-difluoro1,3-benzodioxol-5-yl) ketone, 6.3 grams (0.126 mole) of hydrazine hydrate, and 1.0 mL of acetic acid in 100 mL of ethanol. The yield of (4-trifluoromethylsulfonyloxyphenyl) (2,2-difluoro-1,3-benzodioxol-5-yl) ketone hydrazone was 9.8 grams. The nmr spectrum was consistent with the proposed structure.

The N'-optionally substituted (substituted-phenyl)-(benzoheterocyclyl) ketone hydrazone derivatives of the present invention were tested for insecticidal activity in foliar evaluations against the beet armyworm (*Spodoptera exioua* (Hubner)), southern armyworm (*Spodopters eridania*), and the Mexican bean beetle (*Epilachna varivestis*).

In tests to determine activity against insects on foliage (see Table 2 below), six to ten-day-old pinto bean (*Phaseolus vuloaris*) plants were sprayed to runoff on both upper and lower leaf surfaces with acetone:water solutions containing from 1.0 to 1000 ppm of test chemical. The 10% acetone-water solvent used to prepare the solutions of test chemical contained one drop of surfactant per 100 mL of solvent. Two plants for each insect species and test chemical were sprayed and then transferred to a hood where they were kept until the spray had dried.

In testing activity against Mexican bean beetle, beet armyworm and southern armyworm, two pinto bean plants treated with test chemical as described above were removed from their pots by cutting the stem just above the soil line. The excised leaves and stems from each plant were placed in individual 3-ounce paper cups. Ten third instar larvae were placed in each cup. An opaque plastic lid was placed on each cup, which was then held for the desired exposure period (48 or 96 hours) at 26° C. and 50% relative humidity. At the end of the exposure period the cups were opened and the numbers of dead and live insects were counted. Using the insect counts, the efficacy of the test chemical was expressed in percent mortality.

The data summarizing the results of these tests are set forth in Table 2.

TABLE 2

| Cmpd. No. | Rate (ppm) | Time (Hr) | % Kill[a] MBB | SAW | BAW |
|---|---|---|---|---|---|
| 1 | 500 | 96 | 0 | 0,40 | |
| 2 | 500 | 48 | | 100 | |
| 3 | 500 | 48 | | 70 | |
| 4 | 500 | 48 | | 90 | |
| 5 | 500 | 96 | 0 | 75 | |
| 6 | 500 | 48 | | 35 | |
| 7 | 500 | 96 | 100 | 100 | |
| 8 | 500 | 48 | | 60 | |
| 9 | 500 | 48 | | 100 | |
| 10 | 500 | 48 | | 80,100 | |
| 11 | 500 | 48 | | 85 | |
| 12 | 500 | 48 | | 100 | |
| 13 | 500 | 48 | | 95 | |
| 14 | 500 | 96 | 20 | 85 | |
| 15 | 500 | 96 | 40 | 100 | |
| 16 | 500 | 96 | 75 | 100 | |
| 17 | 500 | 48 | 90 | 100 | |
| 18 | 500 | 48 | 70 | 100 | |
| 19 | 500 | 48 | | 100 | |
| 20 | 500 | 48 | 0 | 100 | |
| 21 | 500 | 96 | 100 | 100 | 100 |
| 22 | 500 | 48 | | 90 | |
| 23 | 500 | 48 | | 95 | |
| 24 | 500 | 48 | | 100 | |
| 25 | 500 | 48 | | 100 | |
| 26 | 500 | 48 | | 75 | |
| 27 | 500 | 48 | | 100 | |
| 28 | 500 | 48 | | 100 | |
| 29 | 500 | 48 | | 95 | |
| 30 | 500 | 48 | | 95 | |
| 31 | 500 | 48 | | 100 | |
| 32 | 500 | 48 | 5 | 12 | |
| 33 | 500 | 48 | | 70 | 15 |
| | 500 | 96 | 5 | | 100 |
| 34 | 500 | 96 | | | 50 |
| 35 | 500 | 96 | | 100 | |
| 36 | 500 | 96 | 0 | 100 | |
| 37 | 500 | 48 | | 65 | |
| 38 | 500 | 48 | | 50 | |
| 39 | 500 | 96 | 90 | | |
| 40 | 500 | 96 | 50 | 100 | |
| 41 | 50 | 96 | 85 | 0 | |
| 42 | 500 | 96 | 50 | | |
| 43 | 500 | 48 | | 60 | |
| 44 | 500 | 48 | | 50 | |
| 45 | 500 | 96 | | 90 | |
| 46 | 500 | 96 | | 75 | |

[a]MBB = Mexican bean beetle, SAW = southern armyworm, BAW = beet armyworm.

We claim:

1. A benzoheterocyclyl ketone hydrazone compound of the formula $$\underset{R^1}{\underset{\|}{\overset{N-NHR^2}{\text{Ar-C-Ar}}}} \overset{Y(CH_2)_n}{\underset{O}{\diagdown}} \overset{R^3}{\underset{R^4}{\diagup}} \quad I$$

in which:

A. Y is methylene, n is 0, $R^3$ and $R^4$ are methyl; $R^1$ is chloro, fluoro, methylsulfonyloxy, or trifluoromethylsulfonyloxy; and $R^2$ is selected form hydrogen, $C_1$-$C_3$ alkylcarbonyl, phenylcarbonyl, halophenylcarbonyl, ethoxycarbonyl, 4-chlorophenylaminocarbonyl, phenylsulfonyl, phenoxycarbonyl, 4-methylphenylcarbonyl, formyl, and trifluoromethylcarbonyl; or B. Y is difluoromethylene, n is 0, $R^1$ is methylsulfonyloxy or trifluoromethylsulfonyloxy, $R^3$ and $R^4$ are fluoro, and $R^2$ is $C_1$-$C_3$ alkylcarbonyl or formyl.

2. The compound of claim 1 in which Y is methylene.

3. The compound of claim 2 in which $R^2$ is ethoxycarbonyl or trifluoromethylcarbonyl.

4. An insecticidal composition comprising an insecticidal amount of a compound of claim 1 in admixture with at least one agriculturally acceptable vehicle, diluent or carrier.

5. The insecticidal composition of claim 4 in which there is employed a compound in which Y is methylene.

6. The insecticidal composition of claim 5 in which there is employed a compound in which $R^2$ is ethyoxycarbonyl or trifluoromethylcarbonyl.

7. A method for controlling insects which comprises applying to the above-ground portions of growing plants an insecticidal amount of a compound of claim 1.

8. The method of claim 1 in which there is employed a compound in which Y is methylene.

9. The method of claim 8 in which there is employed a compound in which $R^2$ is ethoxycarbonyl or trifluoromethylcarbonyl.

* * * * *